United States Patent
Hopka et al.

(10) Patent No.: US 8,627,645 B2
(45) Date of Patent: Jan. 14, 2014

(54) EMISSION CONTROL WITH A PARTICULATE MATTER SENSOR

(75) Inventors: Michael Hopka, Milford, MI (US); Michiel J. Van Nieuwstadt, Ann Arbor, MI (US); Robert F. Novak, Farmington Hills, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 227 days.

(21) Appl. No.: 13/115,713

(22) Filed: May 25, 2011

(65) Prior Publication Data

US 2011/0265551 A1 Nov. 3, 2011

(51) Int. Cl.
*F01N 3/00* (2006.01)
*F01N 3/02* (2006.01)
*G01N 7/00* (2006.01)

(52) U.S. Cl.
USPC ............. 60/276; 60/274; 60/295; 60/297; 60/311; 73/28.01; 73/23.33

(58) Field of Classification Search
USPC ............. 60/274, 276, 277, 295, 297, 311; 73/23.33, 28.01, 28.02
See application file for complete search history.

(56) References Cited

U.S. PATENT DOCUMENTS

| 7,609,068 | B2 | 10/2009 | Ripley |
| 8,136,343 | B2 * | 3/2012 | Zawacki et al. ............... 60/276 |
| 2008/0105567 | A1 | 5/2008 | Okayama et al. |
| 2008/0265870 | A1 | 10/2008 | Nair et al. |
| 2009/0056416 | A1 | 3/2009 | Nair et al. |
| 2011/0047978 | A1 | 3/2011 | Zawacki et al. |
| 2011/0047985 | A1 | 3/2011 | Zawacki et al. |
| 2011/0048106 | A1 | 3/2011 | Zawacki et al. |

OTHER PUBLICATIONS

Hagen, Gunter et al., "Conductometric Soot Sensor for Automotive Exhausts: Initial Studies," Sensors, 2010, 10 1589-1598, 10 pages.

* cited by examiner

*Primary Examiner* — Thomas Denion
*Assistant Examiner* — Diem Tran
(74) *Attorney, Agent, or Firm* — Julia Voutyras; Alleman Hall McCoy Russell & Tuttle LLP (57) ABSTRACT

A method for controlling a particulate matter sensor heater is provided. The method includes operating the heater to burn-off soot accumulated on the sensor; and adjusting the heater level based on sensor output generated during the heater operation. In this way, improved heater control can be achieved using the sensor output already available.

16 Claims, 7 Drawing Sheets

| PM SENSOR RESPONSE DURING REGENERATION CYCLE | SENSOR HEATING ADJUSTMENT FOR SUBSEQUENT CYCLE |

910 — PM SENSOR RISES TO MAXIMUM OUTPUT, THEN FALLS TO A MINIMUM OUTPUT THAT IS MAINTAINED WITH THE HEATER OPERATION CONTINUING

912 — HEATER LEVEL APPROPRIATE, NO ADAPTIVE ADJUSTMENT

914 — PM SENSOR RISES TO MAXIMUM OUTPUT, THEN FALLS TOO LITTLE (i.e., DOES NOT DROP LOW ENOUGH EVEN WITH HEATER MAINTAINED ON)

916 — HEATER LEVEL TOO LOW, INCREASE ADAPTIVE ADJUSTMENT

918 — PM SENSOR RISES TO MAXIMUM OUTPUT, THEN FALLS TO THE MINIMUM OUTPUT, BUT RISES FROM THE MINIMUM WITH THE HEATER OPERATION CONTINUING

920 — HEATER LEVEL TOO HIGH, DECREASE ADAPTIVE ADJUSTMENT

EMISSION CONTROL WITH A PARTICULATE MATTER SENSOR

BACKGROUND AND SUMMARY

Engine emission control systems may utilize various exhaust sensors. One example sensor may be referred to as a Particulate Matter (PM) sensor, which indicates PM mass and/or concentration in the exhaust gas. In one example, the PM sensor may operate by accumulating soot particles over time and providing an indication of the degree of accumulation as a measure of exhaust soot levels. Once full, the sensor may be regenerated by removing the stored soot at increased temperatures. The temperature may be regulated via a sensor heater, with current feedback provided to maintain proper temperatures.

The inventors herein have recognized, however, that over-temperature and under-temperature conditions may still occur due to lack of current feedback, or other inaccuracies and variation in operating conditions. For example, changes in exhaust flow temperature can affect sensor temperature to become too high, possibly degrading the sensor, or too low, resulting in ineffective soot removal and thus sensor reading inaccuracies.

As such, at least some of the above issues may be addressed by controlling a particulate matter sensor heater by operating the heater to burn-off soot accumulated on the sensor, and adjusting the heater level based on sensor output generated during the heater operation.

For example, during a soot removal operation, the sensor output can provide insight into the sensor temperature, as opposed to the soot level of the engine exhaust. During sensor burn-off, the conductivity or resistivity of the sensor may change with the temperature of the sensor thus enabling the sensor to indicate whether the sensor is operating with the temperature, too high, or too low. In this way, it is possible to operate the heater more efficiently, thus avoiding excess heating that can waste energy (and thus degrade fuel economy) and/or degrade sensor performance.

Note that there are various PM sensor readings that may be used, such as conductivity, resistivity, etc., and further the sensor output may be processed in various ways, such as using pull-up or pull-down circuits, amplifiers, etc.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

The following description relates to a particulate matter (PM) sensor regeneration system, and operation thereof. As described in more detail below, a PM sensor measures the mass or concentration of PM (soot) within an exhaust system of an internal combustion engine. Periodically, particles accumulate on a substrate of the PM sensor, and the sensor must be heated to burn off, oxidize, or otherwise drive-off the accumulated PM. In this way, the PM sensor may be regenerated by controlling the temperature of the PM sensor. During such sensor regeneration cycles, the sensor output no longer indicates soot loading in the exhaust, but rather can be used to determine whether proper regeneration conditions are being maintained. For example, the sensor output can indicate over-temperature and/or under-temperature, which can then be used to control the level of sensor heating to better maintain proper temperature control.

Figure 1:
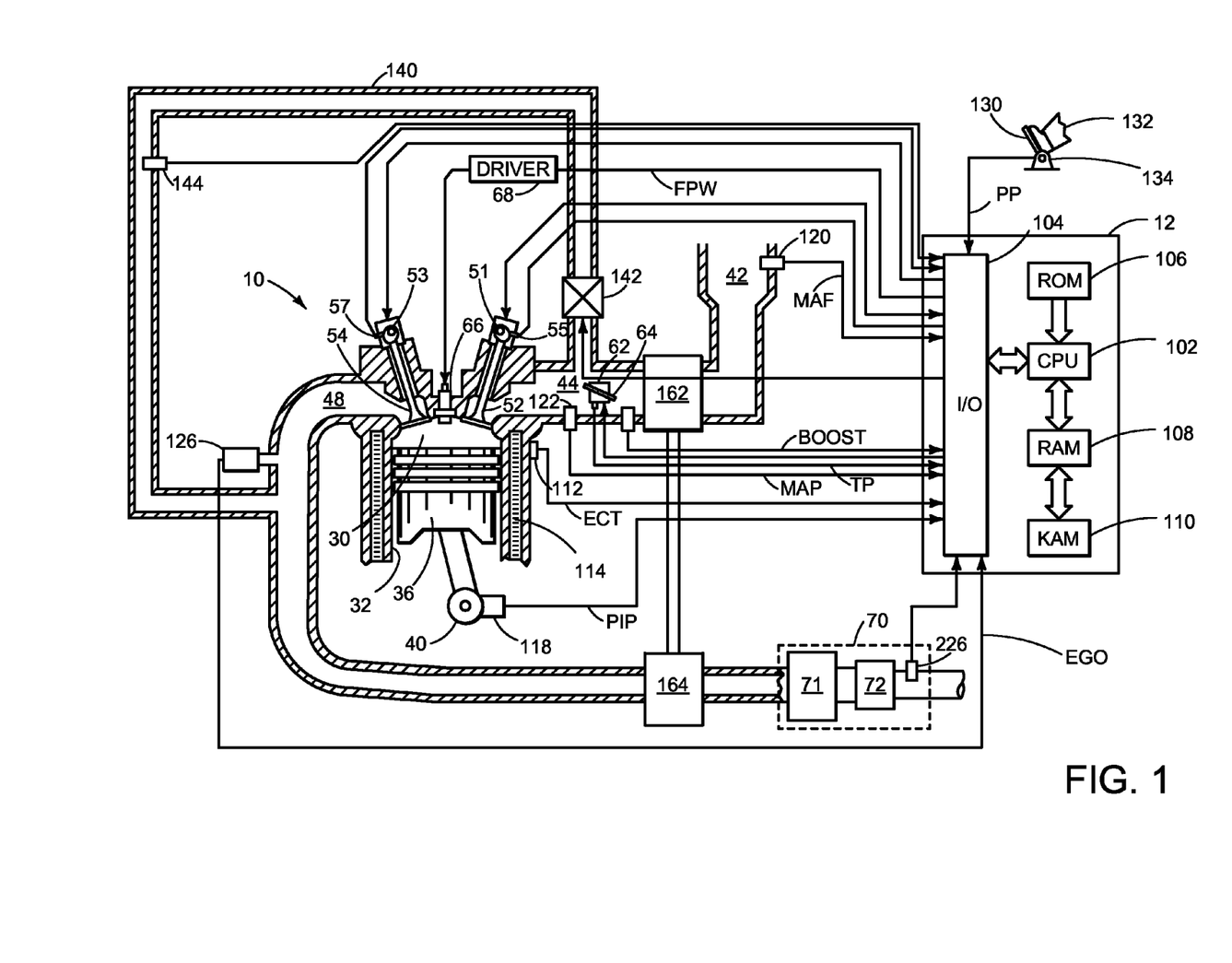
FIG. 1 shows a schematic diagram of an engine.

FIG. 1 is a schematic diagram showing one cylinder of multi-cylinder engine 10, which may be included in a propulsion system of an automobile. Engine 10 may be controlled at least partially by a control system including controller 12 and by input from a vehicle operator 132 via an input device 130. In this example, input device 130 includes an accelerator pedal and a pedal position sensor 134 for generating a proportional pedal position signal PP. Combustion chamber (i.e., cylinder) 30 of engine 10 may include combustion chamber walls 32 with piston 36 positioned therein. In some embodiments, the face of piston 36 inside cylinder 30 may have a bowl. Piston 36 may be coupled to crankshaft 40 so that reciprocating motion of the piston is translated into rotational motion of the crankshaft. Crankshaft 40 may be coupled to at least one drive wheel of a vehicle via an intermediate transmission system. Further, a starter motor may be coupled to crankshaft 40 via a flywheel to enable a starting operation of engine 10.

Combustion chamber 30 may receive intake air from intake manifold 44 via intake passage 42 and may exhaust combustion gases via exhaust passage 48. Intake manifold 44 and exhaust passage 48 can selectively communicate with combustion chamber 30 via respective intake valve 52 and exhaust valve 54. In some embodiments, combustion chamber 30 may include two or more intake valves and/or two or more exhaust valves.

Intake valve 52 may be controlled by controller 12 via electric valve actuator (EVA) 51. Similarly, exhaust valve 54 may be controlled by controller 12 via EVA 53. During some conditions, controller 12 may vary the signals provided to actuators 51 and 53 to control the opening and closing of the respective intake and exhaust valves. The position of intake valve 52 and exhaust valve 54 may be determined by valve position sensors 55 and 57, respectively. In alternative embodiments, one or more of the intake and exhaust valves may be actuated by one or more cams, and may utilize one or more of cam profile switching (CPS), variable cam timing (VCT), variable valve timing (VVT) and/or variable valve lift (VVL) systems to vary valve operation. For example, cylinder 30 may alternatively include an intake valve controlled via electric valve actuation and an exhaust valve controlled via cam actuation including CPS and/or VCT.

Fuel injector 66 is shown coupled directly to combustion chamber 30 for injecting fuel directly therein. Fuel injection may be via a common rail system, or other such diesel fuel injection system. Fuel may be delivered to fuel injector 66 by a high pressure fuel system (not shown) including a fuel tank, a fuel pump, and a fuel rail.

Intake passage 42 may include a throttle 62 having a throttle plate 64. In this particular example, the position of throttle plate 64 may be varied by controller 12 via a signal provided to an electric motor or actuator included with throttle 62, a configuration that is commonly referred to as electronic throttle control (ETC). In this manner, throttle 62 may be operated to vary the intake air provided to combustion chamber 30 among other engine cylinders. The position of throttle plate 64 may be provided to controller 12 by throttle position signal TP. Intake passage 42 may include a mass air flow sensor 120 and a manifold air pressure sensor 122 for providing respective signals MAF and MAP to controller 12.

Further, in the disclosed embodiments, an exhaust gas recirculation (EGR) system may route a desired portion of exhaust gas from exhaust passage 48 to intake passage 44 via EGR passage 140. The amount of EGR provided to intake passage 48 may be varied by controller 12 via EGR valve 142. Further, an EGR sensor 144 may be arranged within the EGR passage and may provide an indication of one or more pressure, temperature, and concentration of the exhaust gas. Alternatively, the EGR may be controlled through a calculated value based on signals from the MAF sensor (upstream), MAP (intake manifold), MAT (manifold gas temperature) and the crank speed sensor. Further, the EGR may be controlled based on an exhaust $O_2$ sensor and/or an intake oxygen sensor (intake manifold)]. Under some conditions, the EGR system may be used to regulate the temperature of the air and fuel mixture within the combustion chamber. While FIG. 1 shows a high pressure EGR system, additionally, or alternatively, a low pressure EGR system may be used where EGR is routed from downstream of a turbine of a turbocharger to upstream of a compressor of the turbocharger.

As such, Engine 10 may further include a compression device such as a turbocharger or supercharger including at least a compressor 162 arranged along intake manifold 44. For a turbocharger, compressor 162 may be at least partially driven by a turbine 164 (e.g. via a shaft) arranged along exhaust passage 48. For a supercharger, compressor 162 may be at least partially driven by the engine and/or an electric machine, and may not include a turbine. Thus, the amount of compression provided to one or more cylinders of the engine via a turbocharger or supercharger may be varied by controller 12.

Exhaust gas sensor 126 is shown coupled to exhaust passage 48 upstream of emission control system 70. Sensor 126 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), a $NO_x$, HC, or CO sensor.

Emission control system 70 is shown arranged along exhaust passage 48 downstream of exhaust gas sensor 126. System 70 may be a selective catalytic reduction (SCR) system, three way catalyst (TWC), $NO_x$ trap, various other emission control devices, or combinations thereof. For example, system 70 may be an SCR system which includes an SCR catalyst 71 and a diesel particulate filter (DPF) 72. In some embodiments, DPF 72 may be located downstream of the catalyst (as shown in FIG. 1), while in other embodiments, DPF 72 may be positioned upstream of the catalyst (not shown in FIG. 1). Emission control system 70 may further include exhaust gas sensor 226. Sensor 226 may be any suitable sensor for providing an indication of a concentration of exhaust gas constituents such as a $NO_x$, $NH_3$, EGO, or PM sensor, for example. In some embodiments sensor 226 may be located downstream of DPF 72 (as shown in FIG. 1), while in other embodiments, sensor 226 may be positioned upstream of DPF 72. For example, sensor 226 may be positioned between SCR 71 and DPF 72, between turbine 164 and SCR 71, and/or upstream of turbine 164. Further, it will be appreciated that more than one sensor 226 may be provided in any suitable position.

As described in more detail with reference to FIG. 2, sensor 226 may be a PM sensor and may measure the mass or concentration of particulate matter downstream of DPF 72. Further, in some embodiments, during operation of engine 10, emission control device 70 may be periodically reset by operating at least one cylinder of the engine within a particular air/fuel ratio.

Controller 12 is shown in FIG. 1 as a microcomputer, including microprocessor unit 102, input/output ports 104, an electronic storage medium for executable programs and calibration values shown as read only memory chip 106 in this particular example, random access memory 108, keep alive memory 110, and a data bus. Controller 12 may receive various signals from sensors coupled to engine 10, in addition to those signals previously discussed, including measurement of inducted mass air flow (MAF) from mass air flow sensor 120; engine coolant temperature (ECT) from temperature sensor 112 coupled to cooling sleeve 114; a profile ignition pickup signal (PIP) from Hall effect sensor 118 (or other type) coupled to crankshaft 40; throttle position (TP) from a throttle position sensor; and absolute manifold pressure signal, MAP, from sensor 122. Engine speed signal, RPM, may be generated by controller 12 from signal PIP. Manifold pressure signal MAP from a manifold pressure sensor may be used to provide an indication of vacuum, or pressure, in the intake manifold. Note that various combinations of the above sensors may be used, such as a MAF sensor without a MAP sensor, or vice versa. During stoichiometric operation, the MAP sensor can give an indication of engine torque. Further, this sensor, along with the detected engine speed, can provide an estimate of charge (including air) inducted into the cylinder. In one example, sensor 118, which is also used as an engine speed sensor, may produce a predetermined number of equally spaced pulses every revolution of the crankshaft.

Storage medium read-only memory 106 can be programmed with computer readable data representing instructions executable by processor 102 for performing the methods described below as well as other variants that are anticipated but not specifically listed.

As described above, FIG. 1 shows only one cylinder of a multi-cylinder engine, and that each cylinder may similarly include its own set of intake/exhaust valves, fuel injector, etc.

Figure 2:
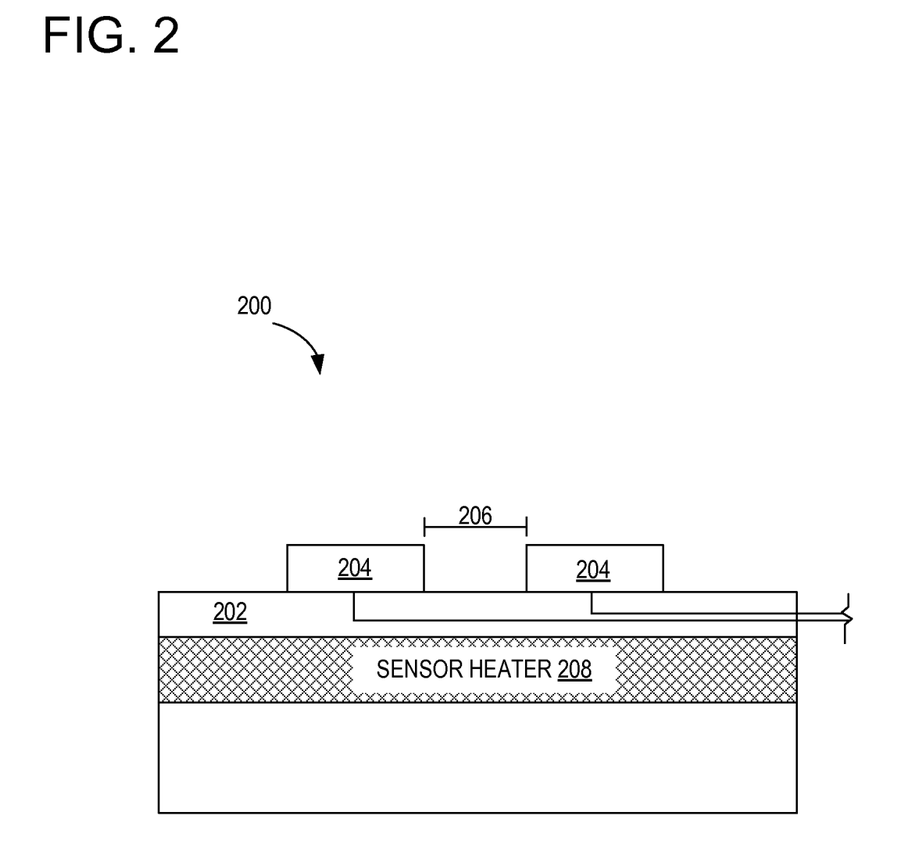
FIG. 2 shows a schematic diagram of a particulate matter sensor.

Referring now to FIG. 2, a schematic view of an example embodiment of a PM sensor 200 is shown. PM sensor 200 may be exhaust gas sensor 226 of FIG. 1 and therefore may share common features and/or configurations as those already described for exhaust gas sensor 226. PM sensor 200 may be configured to measure PM mass and/or concentration in the exhaust gas, and as such, may be coupled to an exhaust pipe. It will be appreciated that sensor 200 is shown in simplified form by way of example and that other configurations are possible.

As shown, PM sensor 200 may include a substrate 202 and two electrodes 204. The substrate 202 may be made of any suitable material. For example, substrate 202 may be a ceramic substrate, although it will be appreciated that other materials are possible.

The two electrodes 204 may be positioned on, or in close proximity to, substrate 202. As shown, the two electrodes 204 may be separated by a small gap, indicated at 206. Electrodes 204 may be non-reactive platinum electrodes, for example, however it will be appreciated that the electrodes may be made of other suitable materials.

A PM sensor design such as that shown in FIG. 2 may lead to soot accumulation on substrate 202 to a point where gap 206 is bridged by the accumulated soot. In such cases, the conductivity between the electrodes 204 drops from the nearly zero conductivity of the ceramic substrate. The conductance between the electrodes is therefore an indication of the cumulative particulate matter in the area of the exhaust that the sensor measures.

PM sensor 200 may be coupled to a PM sensor heater 208, which may be utilized to heat PM sensor 200 to burn off the accumulated soot. In this way, PM sensor 200 may be regenerated. However, as described in more detail below, control of PM sensor heater 208 in terms of temperature is prudent so as not to compromise the integrity of PM sensor 200.

Referring briefly to FIG. 1, controller 12 may receive input data from sensor 200, process the input data, and trigger a response to the processed input data based on instruction or code programmed therein corresponding to one or more routines for regenerating PM sensor 200. Example control routines are described herein with reference to FIGS. 6-9.

It will be appreciated that PM sensor regeneration is different from PM filter regeneration (e.g. DPF regeneration). PM sensor regeneration particularly relates to regeneration of the sensor. In this way, the PM sensor is returned to a condition more suitable for relaying accurate information pertaining to the exhaust. Such information may include diagnostics that relate to the state of the DPF, and thus may at least in part determine if DPF regeneration is warranted. Similar to the PM sensor regeneration described herein, DPF regeneration is typically achieved by raising the temperature of the DPF to a predetermined level, and ensuring that the exhaust gas entering the DPF is of a certain composition.

Turning back to PM sensor regeneration, and as described in more detail below, the PM sensor may utilize a heater to clean off (e.g., burn-off, oxidize, or otherwise remove) accumulated PM and restore the capability of the sensor to indicate exhaust soot levels. Due to highly variable flow and temperature conditions in the engine exhaust, however, the power or heating level used to maintain a desired sensor temperature during soot removal may vary significantly.

In one example as described further herein with regard to FIGS. 6-9, control of the power or heater level to the PM sensor heater can be performed with a feed-forward table which schedules a pulse width modulated (PWM) duty cycle according to the observed or inferred exhaust flow rate and temperature (which is based on engine speed, load, fueling, ignition timing, EGR level, etc). To account for errors in the measured flow and temperature used to schedule the power and also to compensate for part-to-part and shift-over-time variations in the resistance of the heater, an adaptive adjustment may also be used based on the sensor output during soot regeneration, as explained with regard to FIG. 8, for example. Further still, the heater control may also include current monitoring to facilitate adjustment of the power as well, if desired. Alternatively, the system may operate with current monitoring hardware One example adaptation to account for possible errors in the flow and temperature measurements (and/or other errors when scheduling PM sensor heater operation) is based on the sensor outputs or received readings during a sensor regeneration cycle. Such information can then be used to adjust heater operation, such as the heater power level, for improved temperature control and more efficient sensor regeneration as described with regard to FIGS. 3-5.

As described above, the example PM sensor 200 shown in FIG. 2 may accumulate a small amount of soot on a ceramic substrate on which two non-reactive platinum electrodes separated by a small gap are printed. As particles accumulate on the substrate 202, they bridge the gap 206 and cause the conductivity between the electrodes 204 to drop from the nearly zero conductivity of the ceramic substrate. The conductance between the electrodes is therefore an indication of the cumulative PM in the area of the exhaust the sensor measures.

As an accumulating device, the PM sensor eventually fills with so many particles that new particles no longer increase the conductance (or decrease the resistivity). When full, the sensor is heated to either burn or otherwise drive-off the accumulated PM, such as via activation of sensor heater 208 controlled through the PWM voltage that regulates the amount of power delivered to the heater. The sensor temperature can be controlled by the PWM voltage The higher the temperature of the sensor, the faster particles will be removed; however, excessive temperatures can damage the sensor. As such, an adaptation routine may be used. The adaptation routine takes advantage of the electrical properties of the substrate of the PM sensor and the electrodes mounted to it. As the PM sensor heats up, the normally low conductivity of the ceramic substrate in the gap between the electrodes increases. Because of the change in conductivity and the sensor operating principle that PM is driven off the sensor at high temperature, the conductivity of a hot sensor becomes an indicator of the temperature of the element instead of the amount of PM on the sensor. The adaptation uses these principles of sensor operation to detect high or low temperature of the PM sensor during the heating cycle and adapt the heater power over time to reach a desired temperature range.

For example, excessive heater temperature may be detected when the conductivity of the ceramic substrate (measured after PM has been driven from the electrodes yet with the heater still active) exceeds a defined threshold. In these cases, the power to the heater can be decreased, for example in subsequent regeneration cycles at the current operating conditions by a defined increment to drive a lower temperature.

Figure 3:
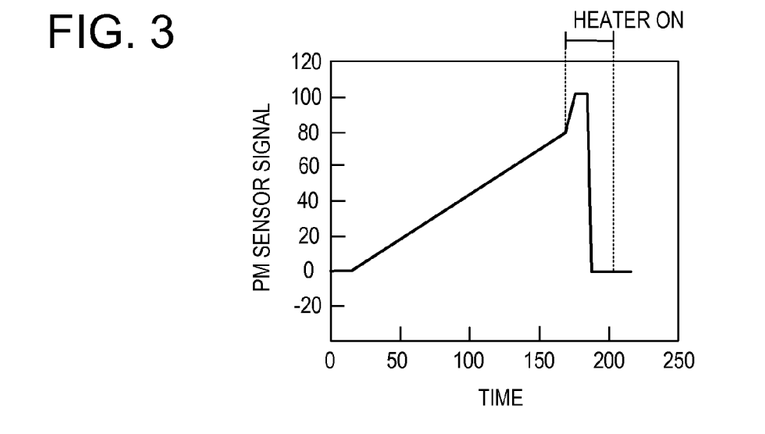
FIG. 3 shows a graph illustrating a particulate matter sensor heater operation indicating a normal temperature range over time.
Figure 4:
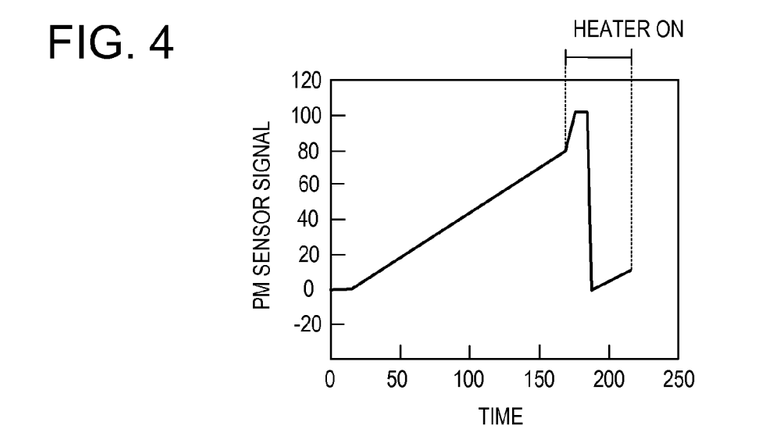
FIG. 4 shows a graph illustrating a particulate matter sensor heater operation indicating a high temperature over time.
Figure 5:
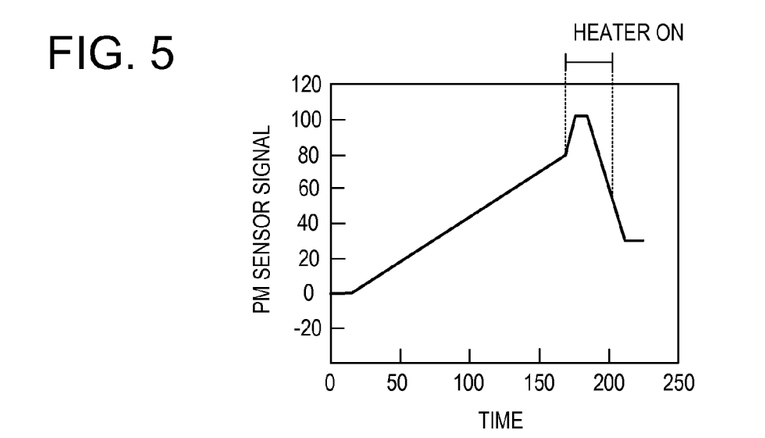
FIG. 5 shows a graph illustrating a particulate matter sensor heater operation indicating a low temperature over time.

Alternatively, the heater temperature may be too low and detected when the accumulated PM is not completely driven off the sensor during sensor heating. This condition is observed as the initially high conductivity of a full sensor failing to return to the near zero value of a clean sensor in a predefined time of heating. In such cases, the power to the heater can be increased by a defined increment to drive a higher temperature in successive sensor cleaning cycles. FIGS. 3-5 demonstrate example normal, high and low temperature observations. As noted above, the examples of FIGS. 3-5 are just one example sensor output signal processing configuration. An alternate configuration may utilize a pull-up style interface circuit in which case the sensor output signals shown in FIGS. 3-5 may be inverted.

Referring now to FIG. 3, it shows a typical particulate matter sensor heater signal response over time. As shown, the sensor signal starts at 0 and has a positive slope as PM accumulates on the electrodes of the sensor. Once the sensor signal reaches approximately 80, the heater is powered on to heat the sensor enough to drive off PM. As indicated, the heater on period is specified, and outside this period the heater is off. As the heater temperature increases, the accumulated PM becomes more conductive, increasing the sensor signal to 100. Once the heater is hot enough, the accumulated PM rapidly oxidizes or diffuses off the sensor. When all PM is removed, the sensor signal returns to 0. After the sensor returns to 0, the heater remains powered to check if the conductivity of the ceramic substrate increases due to heater over-temperature. In this case, the sensor signal with all PM removed and the heater powered is 0, indicating the sensor regeneration temperature is within the appropriate range.

Referring now to FIG. 4, it shows a particulate matter sensor heater signal response operating at an excessively high regeneration temperature over time. As shown, the sensor signal starts at 0 and increases as PM accumulates similar to FIG. 3. At approximately 80, the heater is powered on, increasing PM conductivity until it leaves the sensor. When all PM has been driven from the electrodes, the signal returns to 0. The heater continues to be powered after all PM is gone to check for increases in substrate conductivity. In this case, the sensor signal begins to rise to around 10 because the heater is too hot. As such, the heater adaptation algorithm would detect an over-temperature condition and decrease the heater power for the next sensor regeneration cycle to attempt to lower the heater temperature.

Referring now to FIG. 5, it shows a particulate matter sensor heater signal response operating at an excessively low temperature over time. As shown, the sensor signal starts at 0 and increases as PM accumulates similar to FIGS. 3 and 4. At approximately 80, the heater is powered on, increasing PM conductivity until it leaves the sensor. The PM increases in conductivity as it heats until the sensor is hot enough to begin driving off PM. In this case, PM slowly leaves the surface and after the allowable heating time expires, some PM remains on the sensor. This can be detected by the sensor signal never returning to its initial value after heating. Here, the heater adaptation algorithm will increase the heater power on subsequent regeneration cycles to attempt to increase the heater temperature.

Further, when the temperature is too low, an incomplete regeneration cycle may occur. Thus, not only may the PM sensor heater relay inaccurate readings, but may also lead to more frequent regenerations and less frequent sensor readings. By using a differential reading of the sensor as noted above, it is possible to reduce inaccuracies of incomplete regeneration cycles due to too low of a temperature.

Figure 6:
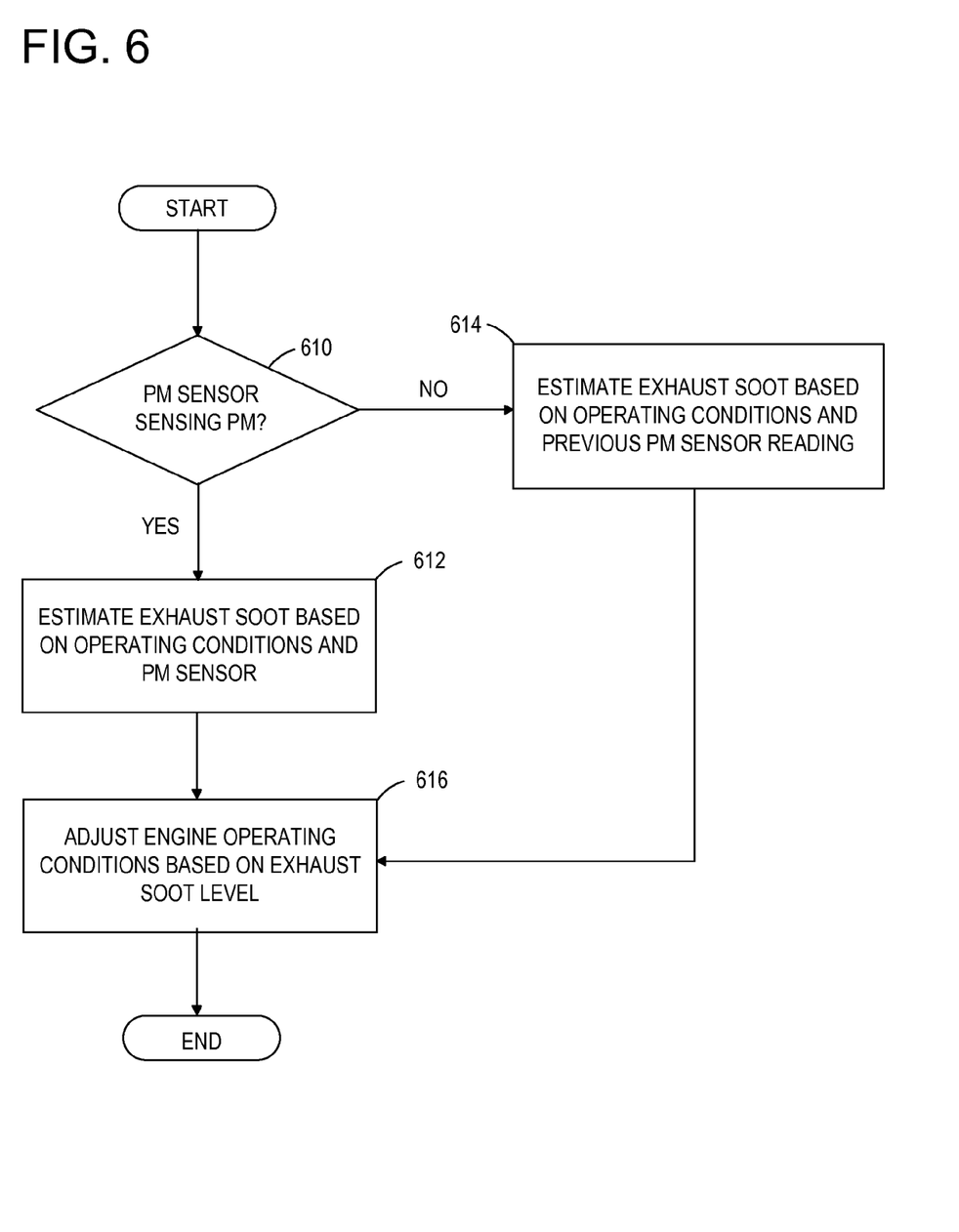
FIG. 6 shows a flow chart illustrating an example method for estimating exhaust soot levels and adjusting engine operation.

Referring now to FIG. 6, a routine is described for estimating exhaust soot levels based on engine operating conditions and a particulate matter sensor reading, and adjusting engine and or vehicle operation and response thereto. First, at 610, the routine determines whether the sensor is sensing exhaust soot levels. For example, the sensor may not be regenerating, the heater may be off, not degraded, the heater may not be fully warmed up, etc. If the answer to 610 is yes, the routine continues to 612 where exhaust soot level is estimated based on the sensor output. In one example, the sensor output is processed through one or more filters, such as a differentiating filter, to indicate the current level of soot in the exhaust flow. The differentiating filter counteracts the integration, or summation of the soot loading that occurs on the sensor so that the sensor output can indicate the instantaneous soot level in the exhaust flow. Addition information and further examples of sensor processing during 612 is provided in FIG. 7, which may operate in coordination with FIG. 6.

Alternatively, if the PM sensor output is not indicative of exhaust soot levels, the routine continues to 614 to estimate the current exhaust soot level based on previous PM sensor readings and an estimate of the change in exhaust soot level since the last PM sensor reading indicative of exhaust soot. The change may be estimated based on various operating conditions, such as engine speed, load, coolant temperature, etc. In this way, even when the PM sensor output is not indicative of the exhaust soot level, previous readings may be used to obtain a more accurate estimate of current exhaust soot levels.

Next, from either 612 or 614, at 616, the routine adjusts engine operation based on the exhaust soot level. For example, the routine may determine whether to regenerate the DPF, adjust the engine fueling to lower exhaust soot levels, etc.

Figure 7:
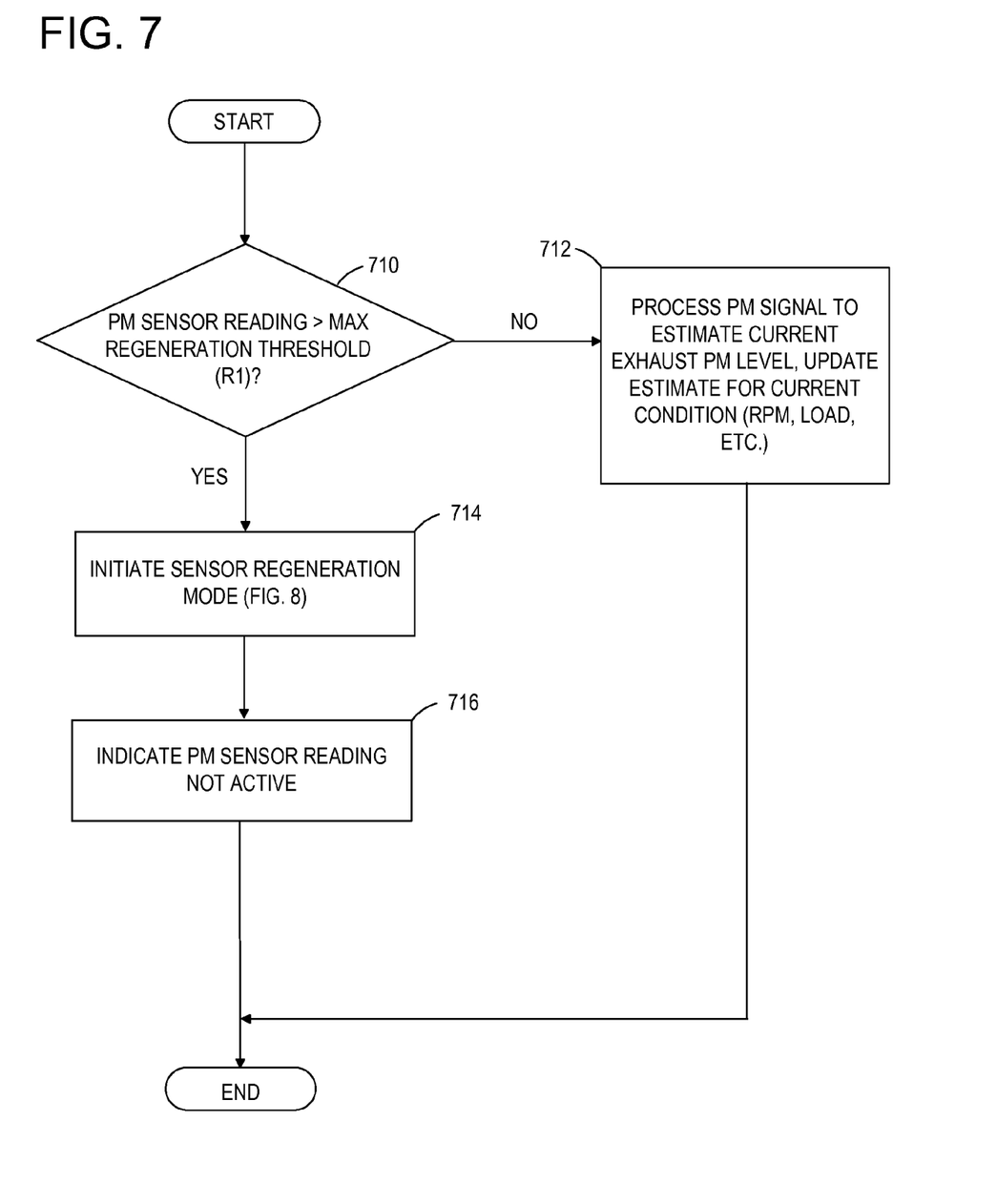
FIG. 7 shows a flow chart illustrating an example method for processing the particulate matter sensor output.

Referring now to FIG. 7, a routine for processing the PM sensor output is provided, as well as for initiating sensor regeneration. First, at 710, the routine determines whether the PM sensor reading indicates a stored soot level on the sensor greater than a maximum regeneration threshold (R1). If so, this indicates that the soot loading onto the PM sensor has reached, or is near reaching, a maximum level beyond which the sensor output can no longer be processed to determine exhaust soot levels. If not, the routine continues to 712 to process the PM sensor output to estimate exhaust soot levels, and to update the estimate for the current operating conditions (see 614). In one example, the PM soot sensor output is differentiated to determine the exhaust soot level. In another example, the routine may estimate the exhaust soot level based on a change in the PM sensor output since a previous reading, and a duration since the previous reading, along with other factors such as the storage efficiency of soot onto the sensor.

Figure 8:
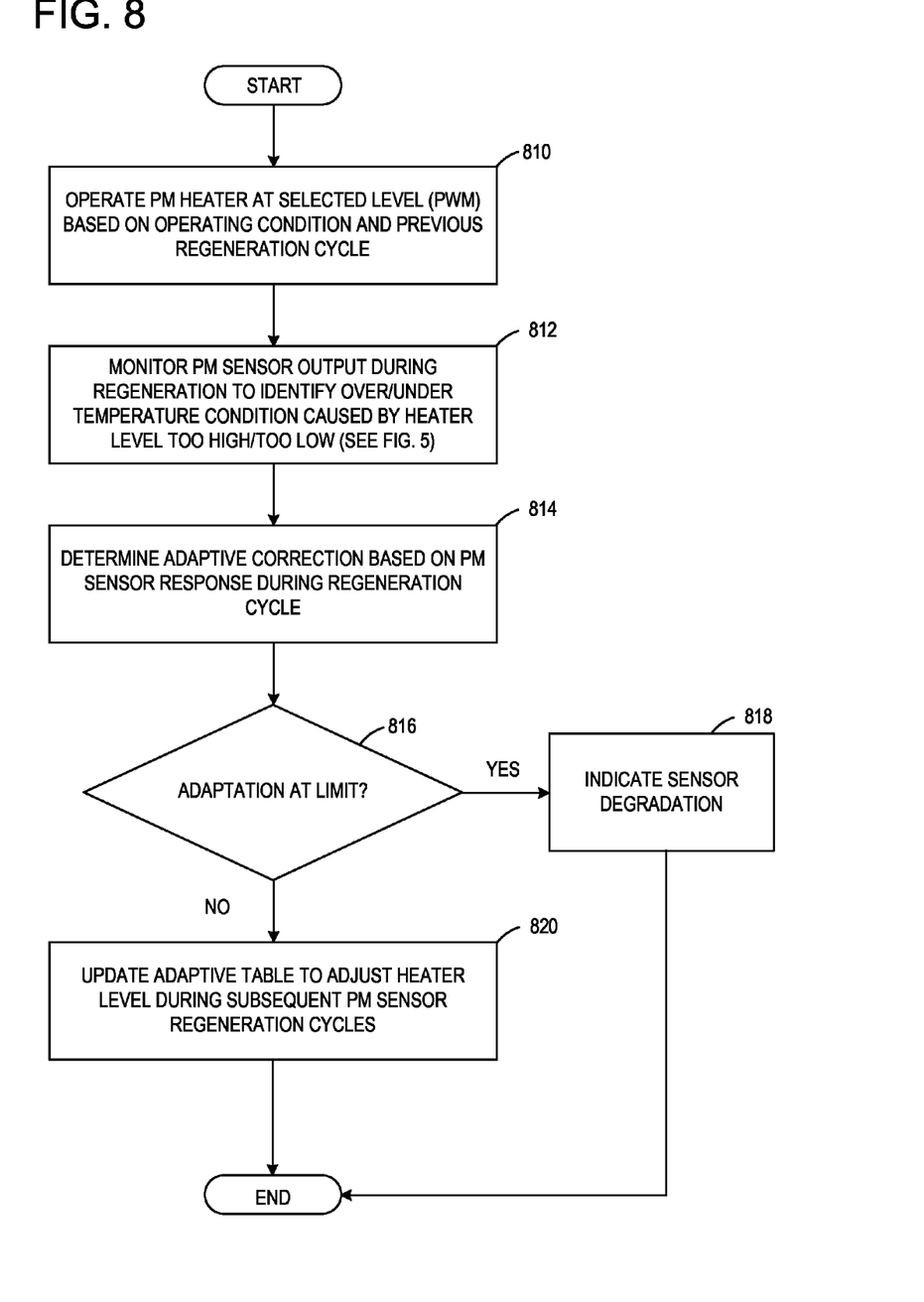
FIG. 8 shows a flow chart illustrating an example method for controlling particulate matter sensor regeneration.

When the answer to 710 is yes, the routine continues to 714 to initiate a PM sensor regeneration cycle, described further herein with regard to FIG. 8. The PM sensor regeneration may be initiated by increasing temperature, such as by increasing exhaust temperature of the engine and/or initiating the PM sensor heater, as explained below herein. Next, at 716, the routine sets a flag to indicate that the PM sensor is inactive in terms of sensing exhaust soot levels.

Continuing with one example approach for PM sensor regeneration, FIG. 8 provides for control of the PM sensor regeneration, as well as learning adaptive corrections for controlling the level of sensor heating to provide a rapid regeneration while reducing over-temperature conditions caused by disturbances to exhaust temperature.

Specifically, at 810, the routine operates the PM heater at a selected PWM setting based on a feed-forward value for current conditions, and an adaptively learned adjustment. The feed-forward value may be based on the current exhaust gas temperature and flow rate. The adaptive adjustment may include information learned from previous PM sensor regeneration cycles as explained herein for the current operating conditions. Again, the adaptive adjustment may be stored based on exhaust gas temperature and flow rate, and/or based on other operating conditions such as engine speed, coolant temperature, engine load, and others. Further, the adaptive adjustment may include both a gain and offset adjustment, for example. The adaptive parameters may be stored in keep-alive memory in one example.

Next, at 812, the routine monitors the PM sensor output during regeneration to identify over/under-temperature conditions caused by external disturbances, drift in the components, erroneous feed-forward commands, etc. As explained previously with regard to FIGS. 3-5, for example, the routine may monitor the PM sensor conductivity during the PM sensor regeneration cycle. The heater operation is maintained during the monitoring. As one example, the routine may monitor for the PM sensor conductivity to rise above a maximum threshold (indicating sensor temperature increasing and commencement of the PM sensor regeneration). Then, when the PM sensor output falls, the routine may monitor whether it falls low enough to a minimum conductivity value (indicating soot burn-off). If not, not enough soot may have been removed due to the temperature too low (and thus the heater PWM level being too low), and the routine may increase the adaptive term(s) for the current set of conditions.

If the sensor conductivity does fall to or below the minimum value (indicating substantially all of the stored soot on the sensor has been removed), the routine further monitors whether the sensor output rises faster than a threshold rate. If so, the temperature is too high, thus indicating that the PWM level is too high. As a result, the routine may decrease the adaptive term(s) for the current set of conditions to result in a lower PWM setting during subsequent PM sensor regeneration cycles at these conditions.

Further still, if the sensor conductivity falls to or below the minimum value and does not rise at too high a rate, or too high a level for a duration following the drop, the routine determines that no adjustment to the adaptive terms is made.

Figure 9:
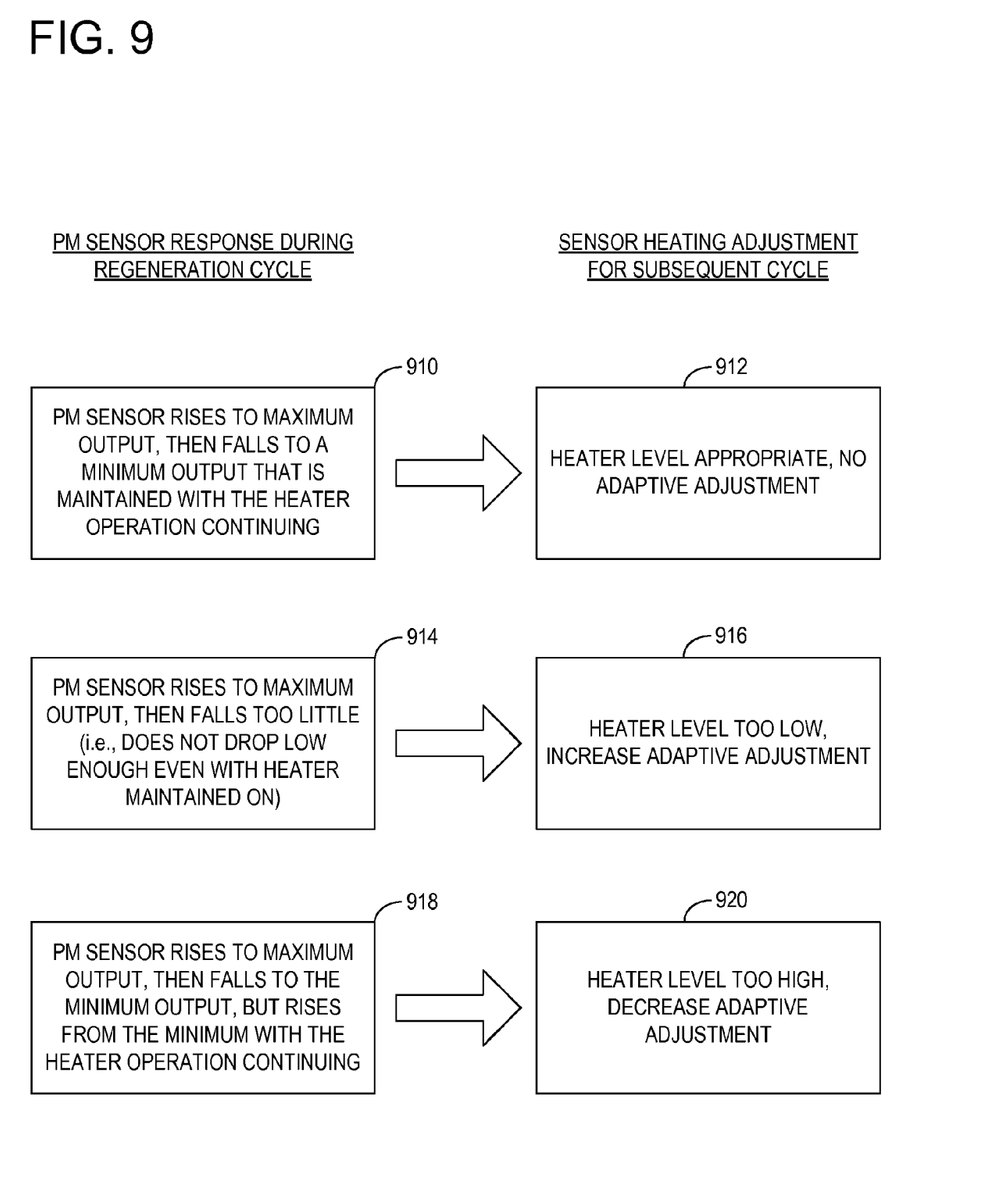
FIG. 9 shows example particulate matter sensor responses and corresponding adjustments.

Additional examples of the determination of 812 are provided with regard to FIG. 9, for example.

Next, at 814, the routine determines the adaptive correction adjustments from 812 based on the degree to which the PM sensor deviated from the expected path.

Continuing with FIG. 8, and 816, the routine determines whether the adaptive corrections have been adjusted to maximum limit values. If so, the routine continues to 818 to set a diagnostic flag indicating degradation in the PM sensor. For example, the routine may set a diagnostic Pcode, illuminate a dashboard light, display a message in a vehicle message center, or combinations thereof. Alternatively, at 820, the routine updates the data stored in keep-alive memory for subsequent PM sensor regeneration at the present set of conditions with the adaptive values determines from 814. For example, the adaptive terms may be indexed as a function of exhaust temperature and flow rate, as one example.

In this way, it is possible to maintain a sufficiently high temperature during PM sensor regeneration in order to reduce the regeneration time, while avoiding over-temperature conditions. Further, it is possible to more fully regenerate the PM sensor during each regeneration cycle, to increase the overall time where the sensor can be used to indicate exhaust soot levels.

As described herein, the various routines of FIGS. 6-8 may operate together, in coordination. FIG. 9 illustrates an overall representation of operation according to the routines of FIGS. 6-8, including adjustments for various example PM sensor responses during a regeneration cycle. As described above, once the PM sensor reaches a high reading, a regeneration cycle is maintained via a sensor heater. Depending on the PM sensor response during the regeneration cycle, the level of sensor heating at subsequent cycles is adjusted accordingly.

At 910, a first example of a PM sensor response during a regeneration cycle is provided. In this example, the PM sensor may rise to a maximum output then fall to a minimum output that is maintained with an ongoing heater operation. In such circumstances, the heater level may be deemed appropriate for the subsequent cycle, and thus, no adaptive adjustment is necessary (as shown at 912).

At 914, another example of a PM sensor response during a regeneration cycle is provided. In this example, the PM sensor may rise to the maximum output then fall too little. Said in another way, the PM sensor response may not drop low enough even with the heater maintained on during a regeneration cycle. As shown at 916, the sensor heater may be adjusted by increasing the adaptive adjustment for a subsequent cycle.

At 918, another example of a PM sensor response during a regeneration cycle is provided. In this example, the PM sensor may rise to the maximum output then fall to the minimum output, but may rise from the minimum with the heater operation continuing during a regeneration cycle. As shown at 920, such a sensor heater response may be too high for the subsequent cycle, and thus the sensor heater may be adjusted by decreasing the adaptive adjustment for a subsequent cycle.

It will be appreciated that an adjustment based on sensor output may be determined in any suitable way without departing from the scope of this disclosure. As an example, an adaptation operation may be configured for a given estimated exhaust flow rate and exhaust temperature (which can be estimated based on speed, load, fuel timing, EGR, coolant temp, et.), determine FF heater PWM level plus modification (gain/offset) based on the current adaptive information for the current conditions. Then, lean adaptation amount for given conditions based on sensor output during the current regeneration cycle at the current flow rate and estimated exhaust temp. Then adjust the current adaptive information based on the sensor output information.

As an example, assuming operating at exhaust temp T1 and exhaust flow rate M1, the FF PWM stored in the table is 50% and the previous learned adjustment was +5%, for example. Then, the regeneration cycle is carried out with 55% PWM and the sensor output monitored. In this case, if the sensor reading indicates too much heater heating, then the adaptive information is adjusted from +5% to +4%, for example. So that on the next sensor regeneration cycle carried out at T1 and M1, the heater then is operated with 54% PWM level.

In this way, an algorithm to detect and compensate the power delivered to a PM sensor that relies upon the electrical properties of the substrate of the PM sensor and the electrodes mounted thereto, can be used to account for possible errors in the flow and temperature measurements used to control PM sensor regeneration.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method for controlling a particulate matter sensor heater, comprising:
   operating the heater to burn off soot accumulated on the sensor; and
   adjusting a heater level based on sensor output generated during heater operation, the heater level adjusted based on the sensor output after a decrease from a peak soot level reading, with the heater active from before the peak reading through and after the decrease.

2. The method of claim 1 wherein the heater level is adjusted based on whether the sensor output fully decreases from the peak to a minimum soot level reading.

3. The method of claim 1 further comprising activating the heater during a sensor regeneration cycle in response to a change in particulate sensor conductivity.

4. The method of claim 3 further comprising decreasing an amount of energy supplied to the heater during a second particulate sensor regeneration cycle in response to conductivity of the particulate sensor increasing after oxidizing soot from the particulate sensor during the sensor regeneration cycle.

5. The method of claim 4 wherein the heater is activated during the sensor regeneration cycle in response to the particulate sensor conductivity reaching a maximum threshold.

6. The method of claim 5 wherein the heater is maintained active throughout the regeneration cycle and while the conductivity increases after oxidizing soot from the particulate sensor during the sensor regeneration cycle.

7. The method of claim 6 further comprising adapting the amount of energy supplied to the heater based on engine operating conditions.

8. The method of claim 7 further comprising adjusting engine operation independent of the sensor conductivity during sensor regeneration cycles.

9. A method for controlling a particulate matter sensor heater, comprising:
   operating the heater to burn off soot accumulated on the sensor; and
   adjusting a heater level based on sensor output generated during heater operation, the heater level decreased when the sensor output fully decreases from a peak soot level output to a minimum soot level output, and then increased from the minimum soot level output, with the heater active from before increasing to the peak soot level through the increase from the minimal soot level output.

10. A system, comprising:
    an engine exhaust with a soot sensor having a heater;
    a controller receiving an output of the soot sensor, and
       during a non-sensor regeneration cycle, adjusting engine operation based on non-regeneration output; and
       during a first sensor regeneration cycle, adjusting engine operation based on the non-regeneration output, activating the heater and receiving a regeneration output from the sensor, and
       during a second sensor regeneration cycle, activating the sensor heater at a level based on the regeneration output received during the first sensor regeneration cycle.

11. The system of claim 10 wherein the soot sensor includes:
    a substrate; and
    two or more electrodes separated by a gap.

12. The system of claim 11 wherein particulate matter accumulates on the substrate such that the particulate matter bridges the gap thereby providing an indication of accumulated soot.

13. The system of claim 11 wherein the substrate is a ceramic substrate and the two or more electrodes are non-reactive platinum electrodes.

14. The system of claim 11 wherein the controller increases or decreases the level based on the regeneration output after soot removal with the heater still active.

15. The system of claim 14 wherein the controller increases the level when the regeneration output does not reach a minimum output.

16. The system of claim 14 wherein the controller decreases the level when the regeneration output increases from a minimum output.

* * * * *